(12) United States Patent
Newby

(10) Patent No.: US 8,813,954 B2
(45) Date of Patent: Aug. 26, 2014

(54) FLUID DISPLACEMENT TISSUE CONTAINER FOR MOLECULAR AND HISTOLOGY DIAGNOSTICS

(75) Inventor: C. Mark Newby, Tuxedo, NY (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1341 days.

(21) Appl. No.: 12/257,101

(22) Filed: Oct. 23, 2008

(65) Prior Publication Data

US 2009/0100944 A1  Apr. 23, 2009

Related U.S. Application Data

(60) Provisional application No. 60/982,038, filed on Oct. 23, 2007.

(51) Int. Cl.
*B65D 25/08* (2006.01)

(52) U.S. Cl.
USPC .......... 206/219; 206/220; 206/221; 220/521; 220/502

(58) Field of Classification Search
USPC .......................... 206/219–221; 220/521, 502
See application file for complete search history.

(56) References Cited

U.S. PATENT DOCUMENTS

| | | |
|---|---|---|
| 4,034,884 A | 7/1977 | White |
| 4,076,592 A | 2/1978 | Bradley |
| 4,220,252 A | 9/1980 | Beall et al. |
| 4,416,984 A | 11/1983 | Wheeler, Jr. |
| 4,903,869 A * | 2/1990 | McKenna .................. 222/449 |
| 6,207,408 B1 | 3/2001 | Essenfeld et al. |
| 7,052,651 B2 * | 5/2006 | Wang ........................ 422/417 |
| 7,147,826 B2 | 12/2006 | Haywood et al. |
| 7,270,959 B2 * | 9/2007 | Hudak ....................... 435/7.1 |
| 7,300,633 B2 * | 11/2007 | Hudak et al. ............... 422/537 |
| 7,438,852 B2 * | 10/2008 | Tung et al. ................. 422/562 |
| 2002/0048819 A1 * | 4/2002 | Alley ........................ 436/169 |
| 2003/0086830 A1 * | 5/2003 | Haywood et al. ........... 422/102 |
| 2004/0038269 A1 | 2/2004 | Birnboim |
| 2005/0163660 A1 | 7/2005 | Wang |
| 2006/0245977 A1 | 11/2006 | Bodner |
| 2008/0025877 A1 | 1/2008 | Alley |

FOREIGN PATENT DOCUMENTS

| | | |
|---|---|---|
| DE | 20201894 U1 | 5/2002 |
| EP | 0332753 A1 | 9/1989 |
| FR | 2612297 A | 9/1988 |

(Continued)

OTHER PUBLICATIONS

U.S. Appl. No. 12/257,057.

(Continued)

*Primary Examiner* — Anthony Stashick
*Assistant Examiner* — Blaine Neway
(74) *Attorney, Agent, or Firm* — The Webb Law Firm

(57) ABSTRACT

A container for storing a biological sample for molecular diagnostic testing and/or histological testing is provided. The container includes a first chamber for receiving a sample holder therein, a second chamber, and a closure for enclosing the container. A transitional barrier, such as a valve, is in fluid communication between the two chambers. The transitional barrier is transitional between a first position in which the first chamber is in fluid isolation from the second chamber, and a second position in which fluid can pass from at least one of the first and second chambers to the other of the first and second chambers.

14 Claims, 16 Drawing Sheets

(56) References Cited

FOREIGN PATENT DOCUMENTS

| | | | |
|---|---|---|---|
| GB | 1234044 | A | 6/1971 |
| JP | 4965889 | | 6/1974 |
| JP | 59113886 | A | 6/1984 |
| JP | 10281953 | A | 10/1988 |
| JP | 06078746 | A | 3/1994 |
| JP | 2000510703 | A | 8/2000 |
| JP | 2001194365 | A | 7/2001 |
| JP | 2003057232 | A | 2/2003 |
| WO | 7901131 | A | 12/1979 |
| WO | 03031065 | A | 4/2003 |
| WO | 03044488 | A1 | 5/2003 |
| WO | 2006041297 | A2 | 4/2006 |
| WO | 2008040812 | A1 | 4/2008 |

OTHER PUBLICATIONS

U.S. Appl. No. 12/257,073.
U.S. Appl. No. 12/257,134.
U.S. Appl. No. 12/257,119.

\* cited by examiner

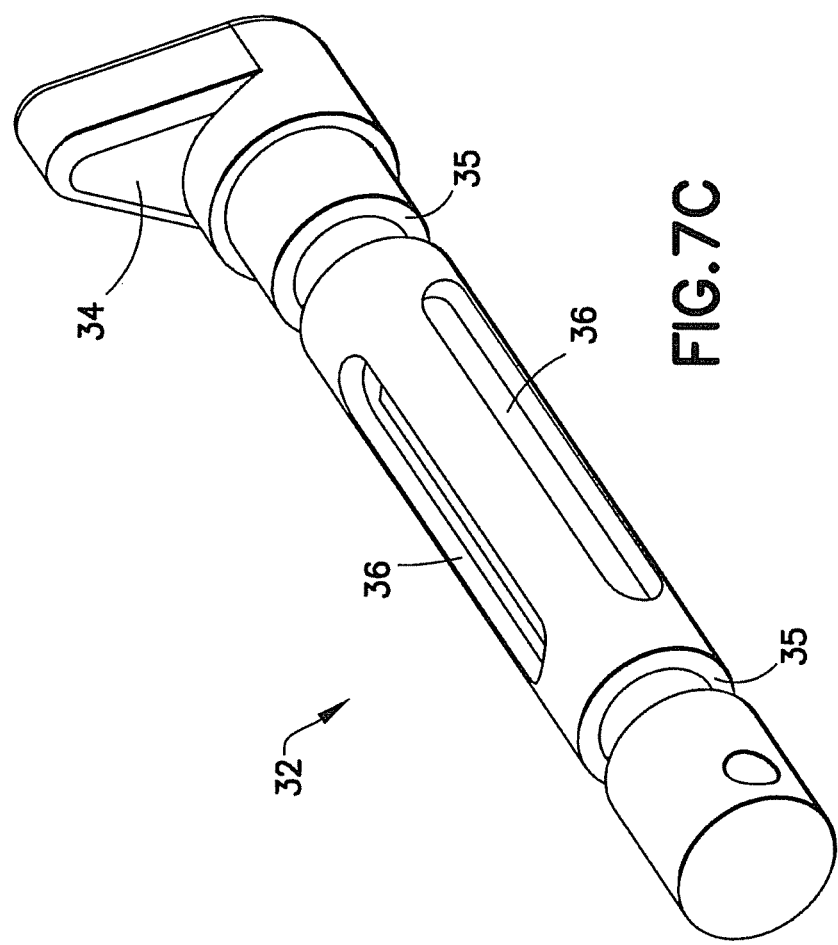

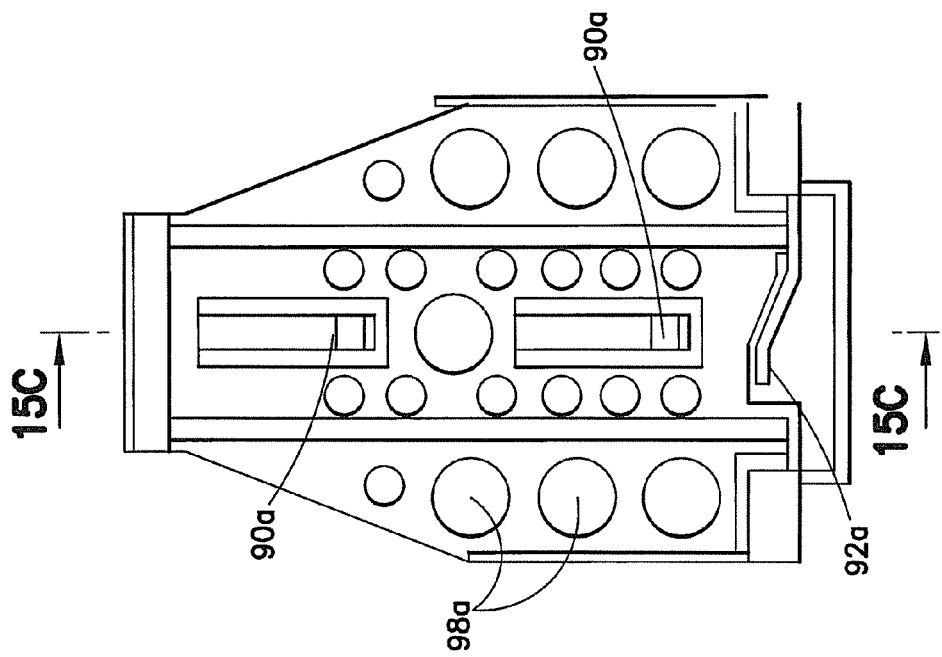
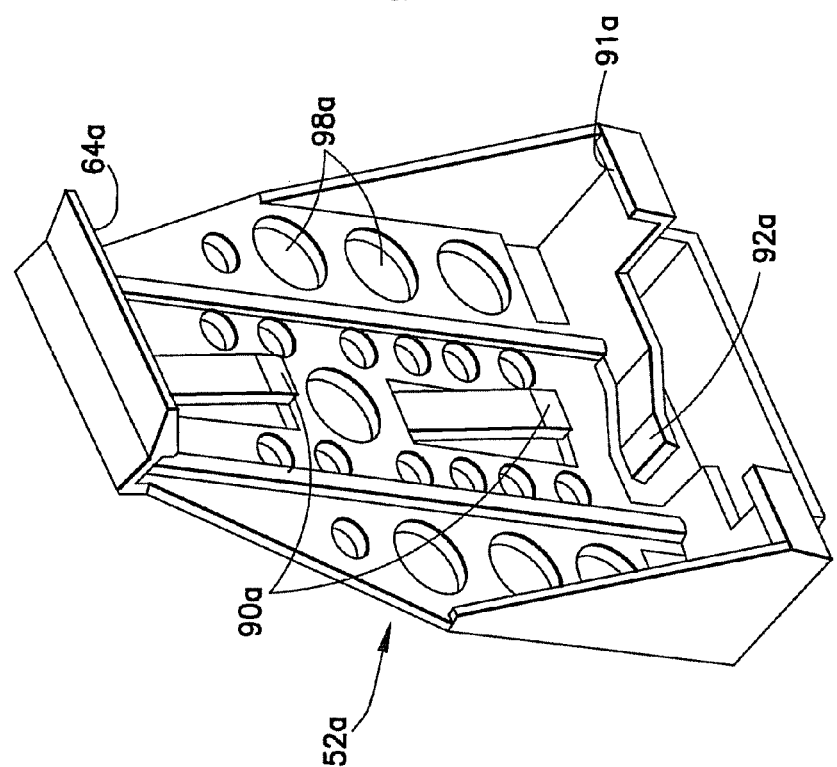

FLUID DISPLACEMENT TISSUE CONTAINER FOR MOLECULAR AND HISTOLOGY DIAGNOSTICS

CROSS REFERENCE TO RELATED APPLICATION

This application claims priority to U.S. Provisional Patent Application No. 60/982,038, filed Oct. 23, 2007, entitled "Fluid Displacement Tissue Container For Molecular and Histology Diagnostics", the entire disclosure of which is herein incorporated by reference.

BACKGROUND OF THE INVENTION

1. Field of the Invention

The present invention relates to a tissue sample container. More particularly, the present invention relates to a sample container for containing a biological tissue specimen for molecular diagnostic testing and/or histological testing.

2. Description of Related Art

Biological samples are often obtained by a researcher or clinician for diagnostic evaluation to determine the presence of certain diseases and to determine an appropriate treatment for the disease. Tissue samples are often obtained from a patient for molecular diagnostic and nucleic acid analysis, particularly RNA and DNA analysis, which have become common place in research for the treatment of numerous diseases. An essential requirement for accurate RNA and DNA analysis is the presence of high quality and intact RNA and DNA within the biological sample.

Oftentimes, the histologic or cytologic analysis will be performed immediately after the sample is removed from the patient or source to avoid molecular changes that may occur during storage. These changes, such as gene transcription, result from the degradation of the nucleic acids within the sample caused by exposure of an untreated sample to certain environmental stresses. However, analysis of the sample immediately after the sample is collected is often impossible or impractical. Therefore, it is necessary to provide a system for storing a sample under controlled conditions for a certain period of time while maintaining the structural and molecular integrity of the sample.

Traditionally, one way of accomplishing this storage is by submerging the sample in a single fixative reagent. A typical fixative reagent is 10 percent (%) formalin but may also include water, miscible alcohols, ethanol/acetone mixtures, and ethanol/acetic acid mixtures. The containers used for such storage are generally composed of a single integral cavity which could house an effective volume of reagent to treat a particular biological tissue sample. The biological tissue sample is placed in the container along with the reagent, the container is closed, and the sample is then stored and transported while being preserved by the fixative agent. An example of such a container can be seen in U.S. Pat. No. 7,147,826 to Haywood et al. Such containers have experienced some success in the industry, but are subject to certain limitations.

SUMMARY OF THE INVENTION

In an embodiment of the present invention a container for storing a biological sample includes a first chamber having an open end, structured to receive a fluid, and a sample holder at least partially therein. The container also includes a second chamber adapted to receive a fluid therein, and a closure for enclosing at least the open end of the first chamber. A transitional barrier is disposed at least partially between the first chamber and the second chamber. The barrier is transitional from a first position in which the first chamber is in fluid isolation from the second chamber, to a second position in which fluid can pass from at least one of the first chamber and the second chamber to the other of the first chamber and the second chamber.

The sample holder may be detachably connected to the closure. Optionally, the sample holder is rotatable with respect to the closure. In one configuration, a platform is attached to the closure and is adapted for receiving the sample holder. The platform may be rotatable with respect to the closure. The sample holder may include a closable housing defining an internal cavity for holding a biological sample. The housing of the sample holder may also include a plurality of fluid openings for allowing fluid contained within at least one of the first chamber and the second chamber to pass into the internal cavity. In a particular configuration, the sample holder is a histology cassette.

The first chamber may have a first intended fill volume, and the second chamber may have a second intended fill volume that is different than the first intended fill volume. In a further configuration, a first fluid may be disposed within the first chamber and a second fluid may be disposed within the second chamber, with the first fluid being different than the second fluid. In a further configuration, the transitional barrier is a valve. The valve may have a handle for allowing movement of the valve between the first position and the second position.

The first chamber may include a first housing and the second chamber may include a second housing. The first housing may be at least partially insertable within the second housing, thereby causing fluid within the second housing to displace into the first housing through the valve. The valve may be a one-way valve permitting fluid flow from the second housing into the first housing. The first housing may also include a vent for venting from the first chamber upon displacement of fluid from the second housing into the first housing.

In another embodiment, the present invention is directed to a container for storing a biological sample. The container includes a housing extending between a first open end and a second end, with the first open end defining a first chamber adapted to receive a fluid and a sample holder therein. The housing further includes a second chamber adapted to receive a fluid therein and a closure for enclosing at least the open end of the housing. A valve extends between the first and second chambers and is movable between a first position in which the first chamber is in fluid isolation from the second chamber to a second position in which fluid can pass from at least the second chamber into the first chamber.

Optionally, the sample holder is removably connected to the closure and extends from the closure into the first chamber. The sample holder may define an internal cavity for holding a biological sample. The sample holder may include at least one fluid opening adapted for allowing fluid contained within at least one of the first chamber and the second chamber to pass into the internal cavity. The closure and the housing may be removably provided in threaded engagement. In a further configuration, the sample holder is rotatable with respect to the closure and the first chamber of the housing. The valve may further include a handle for movement of the valve between the first position and the second position.

In accordance with yet another embodiment of the present invention, a container for storing a biological sample includes a first housing defining a first chamber and including an open end having a closure removably engaged thereover. The first chamber is adapted to receive a sample holder therein. The container also includes a second housing defining a second chamber adapted to contain a fluid therein and to receive at least a portion of the first housing therein. At least one of the first housing and the second housing further includes a valve for permitting fluid from the second chamber to move into the first chamber and contact the sample holder received within the first chamber upon insertion of at least a portion of the first housing into the second chamber.

In a further configuration, the valve is a one-way valve associated with the first housing and permitting fluid flow into the first chamber. The first housing may also include a vent for venting from the first chamber upon movement of fluid from the second chamber into the first chamber. Optionally, the first chamber is further adapted to receive a first fluid therein, the first fluid being different than the fluid within the second chamber.

In yet another embodiment of the present invention, a method of storing a biological sample within at least one liquid includes the step of providing a container having a first chamber having an open end, and a second chamber, isolated from the first chamber, and containing a liquid therein. The method also includes the step of inserting a sample holder containing a biological sample into the first chamber. The method further includes the step of establishing fluid communication between the first chamber and the second chamber such that the liquid contained within the second chamber contacts the biological sample disposed within the first chamber.

The first chamber may contain a first liquid, and the step of establishing fluid communication between the first chamber and the second chamber may further include the step of opening a valve between the first chamber and the second chamber. The step of establishing fluid communication between the first chamber and the second chamber may also include transitioning a transitional barrier disposed between the first chamber and the second chamber from a first position, in which the first chamber is in fluid isolation from the second chamber, to a second position in which fluid may pass between the first chamber and the second chamber. In a further configuration, the transitional barrier is a valve.

BRIEF DESCRIPTION OF THE DRAWINGS

FIG. 7C is a perspective view of a valve component for use in the container of FIG. 1.

FIG. 15A is a perspective view of an alternate embodiment of a platform for use in connection with the present invention.

FIG. 15B is a front view of the platform of FIG. 15A.

DESCRIPTION OF PREFERRED EMBODIMENTS

Figure 1:
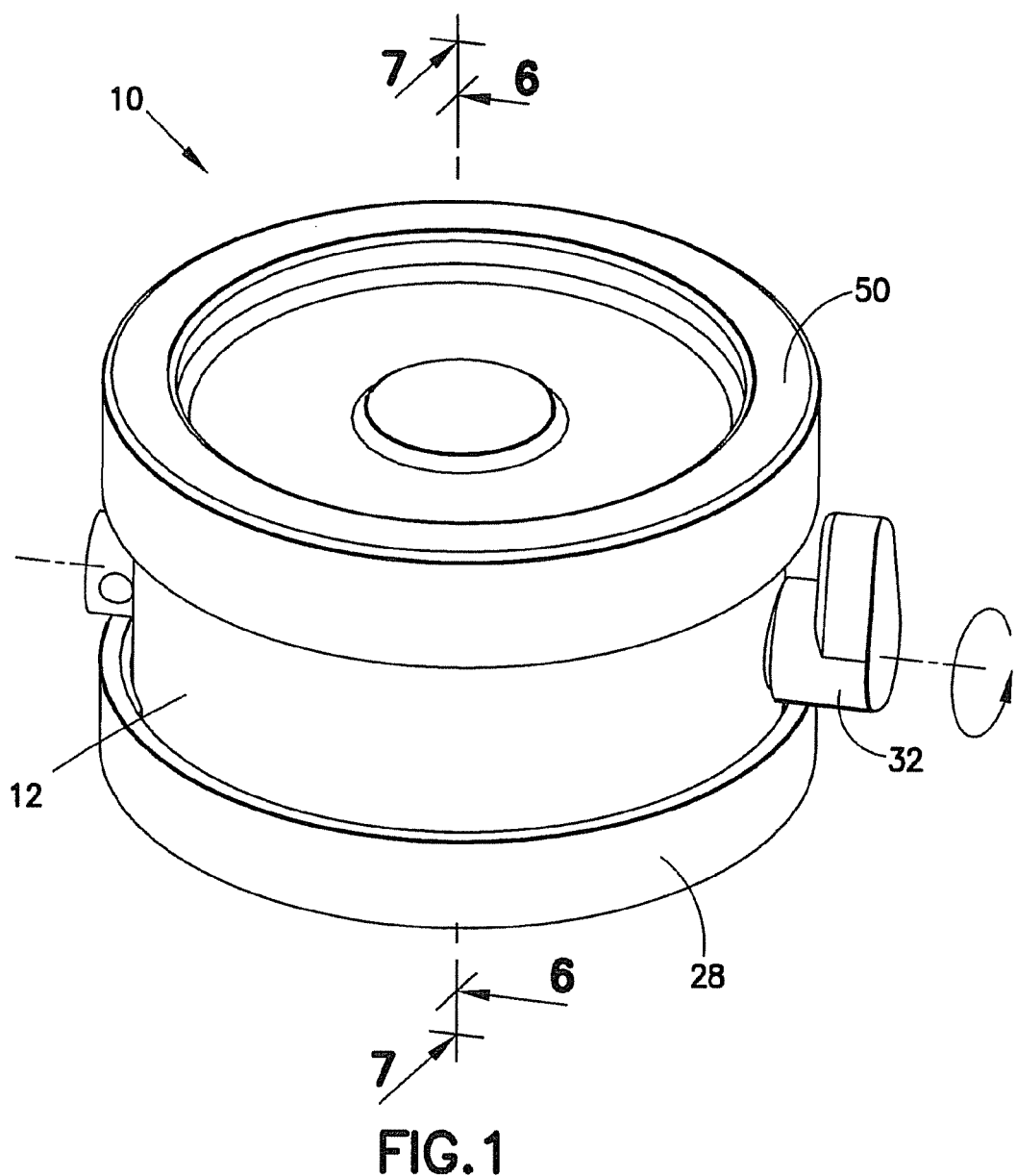
FIG. 1 is a perspective view of a container for storing a biological sample in accordance with an embodiment of the present invention.
Figure 2:
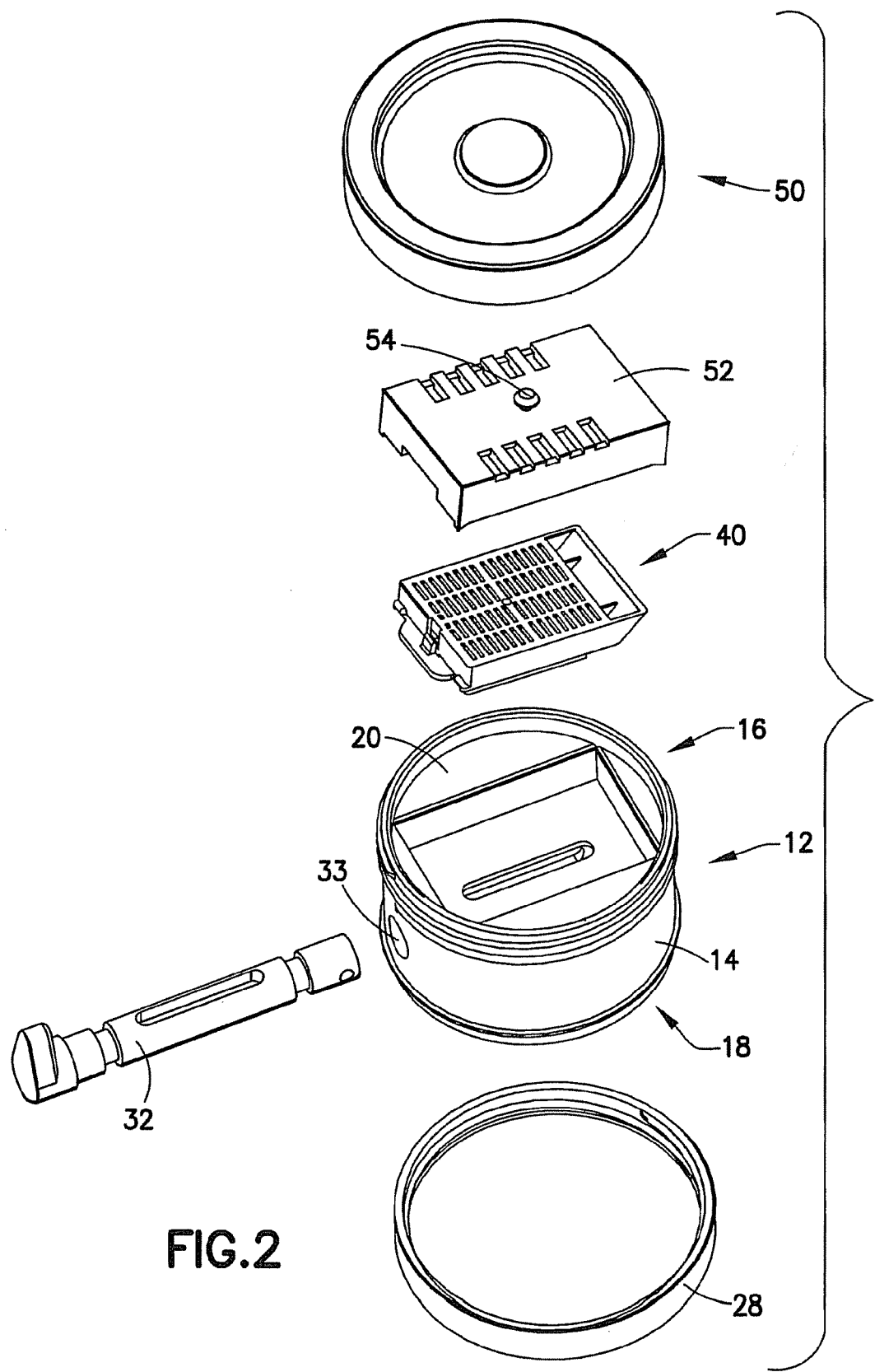
FIG. 2 is an exploded perspective view of the container of FIG. 1.

For purposes of the description hereinafter, spatial orientation terms, if used, shall relate to the referenced embodiments as oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

The container of the present invention allows for storage of a biological sample, such as a tissue sample for molecular and histology diagnostics, and in particular histopathology testing. In particular, the container includes a first chamber and a second chamber in fluid isolation from each other. A transitional barrier isolates the first chamber from the second chamber, and is transitional between a first orientation where the first chamber is in fluid isolation from the second chamber and a second orientation where fluid can pass at least in one direction between the first and second chambers. Accordingly, a liquid medium may be contained in at least one of the chambers, such as the second chamber. In this manner, a tissue sample contained in, for example, the first chamber may be handled or processed prior to contacting the tissue with the solution in the second chamber. As will be discussed in greater detail herein, in one embodiment of the invention, the first chamber may be empty representing a storage chamber, and the second chamber may include a liquid medium, such as a reagent in the form of a tissue fixative solution for fixing a sample for histopathology diagnostics. In this manner, a tissue sample may be placed within the first chamber, and when desired, the barrier separating the first and second chamber may be transitioned so as to place the tissue sample in fluid contact with the solution within the second chamber.

In a further embodiment of the invention, the first chamber may contain a first fluid, such as a tissue fixative solution, and the second chamber may contain a second fluid, such as a reagent in the form of a protein stabilization solution, such that a tissue sample may be placed in the first chamber in fluid contact with the first fluid for a desired time period, after which the barrier separating the first chamber from the second chamber may be transitioned so as to place the tissue sample in fluid contact with the solution within the second chamber. For example, the fluid flow may occur in only one direction, such that the second fluid may flow from the second chamber into the first chamber and contact the tissue sample directly, along with the first fluid. Alternatively, the first fluid may flow into the second chamber and the mixture of the first and second fluid may flow back into the first chamber, thereby permitting the second fluid to contact the tissue sample, along with the first fluid. The embodiments described herein are representative of containers capable of use in any of these manners.

Referring to the drawings, in which like reference characters refer to the like parts throughout the several views thereof, FIGS. 1-7C illustrate a container 10 in accordance with an embodiment of the present invention. Generally, container 10 includes a housing 12, a first chamber 20, a second chamber 26, a valve 32, a closure 50, and a sample holder 40. The individual components of container 10 may be made of any suitable material that is impervious to liquid and/or gas, such as glass and/or plastic. In one embodiment, the housing 12 may be made of one or more than one of the following representative materials: polypropylene, polyethylene terephthalate (PET), glass, or combinations thereof.

Container 10 generally includes a housing 12 having a housing wall 14 extending between a first open end 16 and a second end 18. Housing wall 14 defines first chamber 20, with first open end 16 extending into the first chamber 20. First chamber 20 defines a first intended fill volume and may include a cavity that may be sized so as to receive and accommodate sample holder 40 therein, as will be discussed in more detail. For example, first chamber 20 may include a bottom wall surface 22 and side wall surfaces 24a, 24b, 24c, and 24d defining a generally rectangular shaped cavity generally corresponding to the size and shape of sample holder 40.

Housing wall 14 further defines second chamber 26 defining a second intended fill volume, which is desirably different than the first intended fill volume of the first chamber 20. Second chamber 26 may be positioned adjacent second end 18 of housing 12. Second end 18 may be an open end extending into second chamber 26. In such an arrangement, container 10 further includes a cover 28 for mating with housing 12 over the second end 18, thereby providing a closable access to second chamber 26. Cover 28 may be matable with housing 12 in any manner, such as a frictional fit, snap fit, threadable engagement, interlocking structural engagement, or other manner, providing a liquid tight seal. For example, corresponding threads may be provided about the perimeter of an external surface of cover 28 and within the perimeter of an internal surface of housing wall 14 of housing 12 at second end 18, or may be provided within the perimeter of an internal surface of cover 28 and about the perimeter of an external surface of housing wall 14 of housing 12 at second end 18.

Figure 5A:
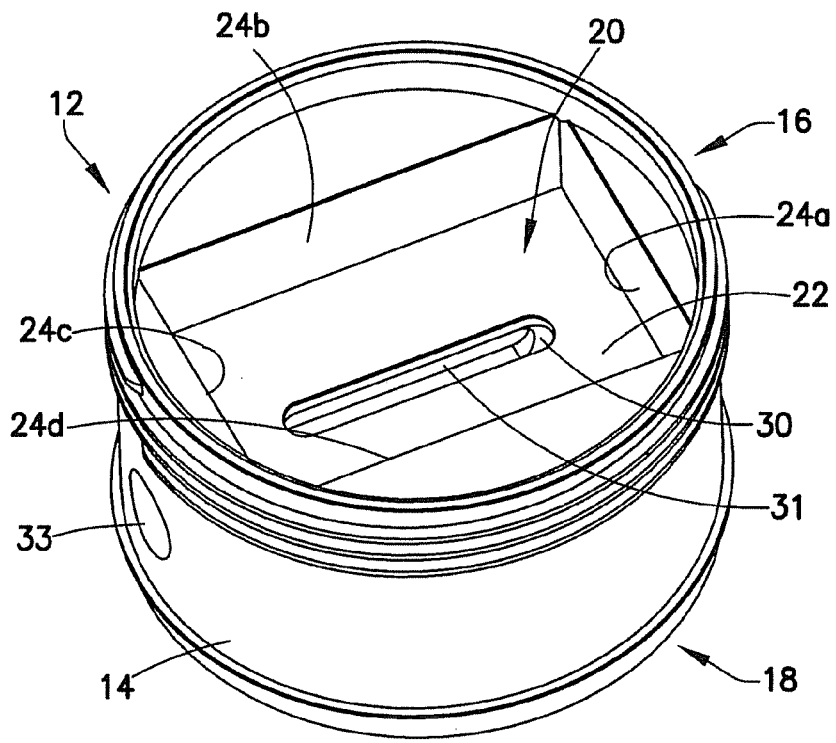
FIG. 5A is a top perspective view of the container housing of the container of FIG. 1.
Figure 5B:
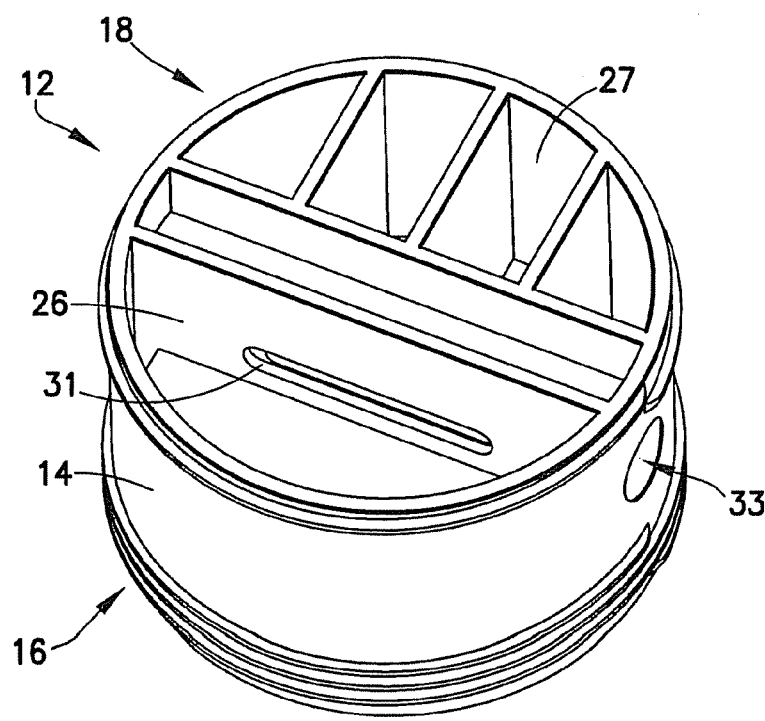
FIG. 5B is a bottom perspective view of the container housing of FIG. 5A.

Second chamber 26 may represent the entire bottom portion of housing 12 extending below bottom wall surface 22 of first chamber 20. Alternatively, as shown in FIG. 5B, second chamber 26 may represent only a portion of the interior of housing 12 at second end 18, with the remaining interior of housing 12 at second end 18 representing dead space 27.

Housing 12 includes structural features such that first chamber 20 and second chamber 26 may be selectively placed in fluid communication with each other. This may be accomplished by providing fluid openings extending between first chamber 20 and second chamber 26. For example, as shown in FIGS. 5A and 5B, first and second openings 30, 31 may extend through bottom wall surface 22 of first chamber 20 and into second chamber 26. In order to selectively place first chamber 20 in fluid communication with second chamber 26, a transitional barrier such as valve 32 may be provided across the openings 30, 31.

For example, valve 32 can extend through housing wall 14 and includes a handle 34 extending externally to housing wall 14 for manual manipulation by a user. Housing 12 may include structural elements for supporting and maintaining valve 32 movably mounted within housing 12, such as interior opening 33 extending across the interior of housing 12, with valve 32 provided as a rotatable structure within interior opening 33 and with handle 34 extending out from at least one side of housing wall 14. Valve 32 may include structural features, such as grooves 35, which correspond with structural elements of housing 12 for providing valve 32 as a rotatable member within interior opening 33. Sealing elements such as o-rings (not shown) may also be provided at the engagement between valve 32 and housing 12, such as within grooves 35 of valve 32, for providing a fluid-tight seal between the valve 32 and housing 12.

Valve 32 further includes at least one channel 36 (shown in FIGS. 6A, 6B, 7A, 7B, and 7C) extending through the body thereof that can be selectively positioned so as to selectively provide fluid communication between first chamber 20 and second chamber 26 upon movement of valve 32 with respect to housing 12. In embodiments where second chamber 26 is vertically offset from first chamber 20 with respect to the longitudinal axis of housing 12 as depicted herein, channel 36 may define an angle, such as a 90 degree angle (seen in FIGS. 6A and 6B), so as to provide fluid communication therethrough between first opening 30 and second opening 31.

Figure 6A:
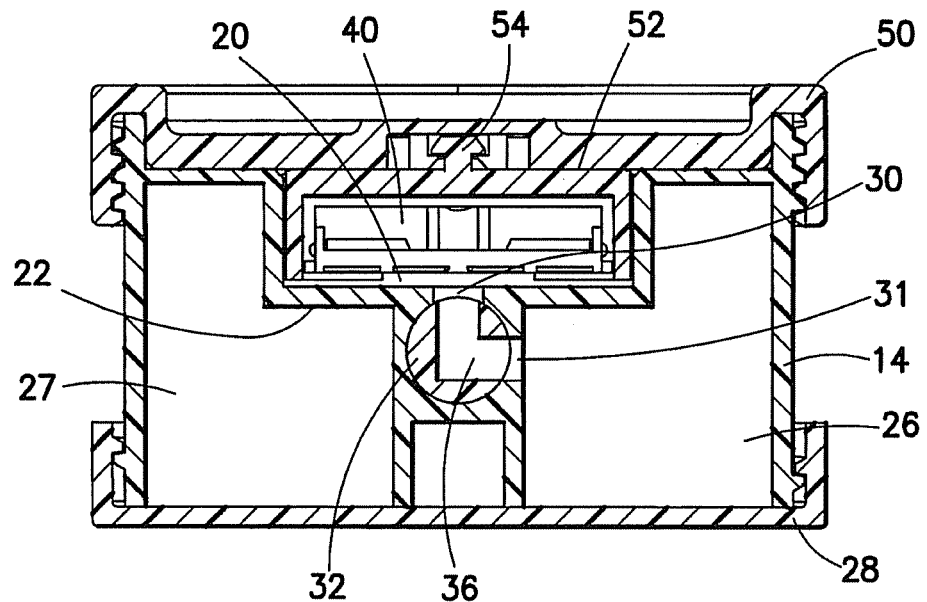
FIG. 6A is a cross-sectional view of the container taken along lines 6-6 of FIG. 1 with the valve depicted in an open position.
Figure 6B:
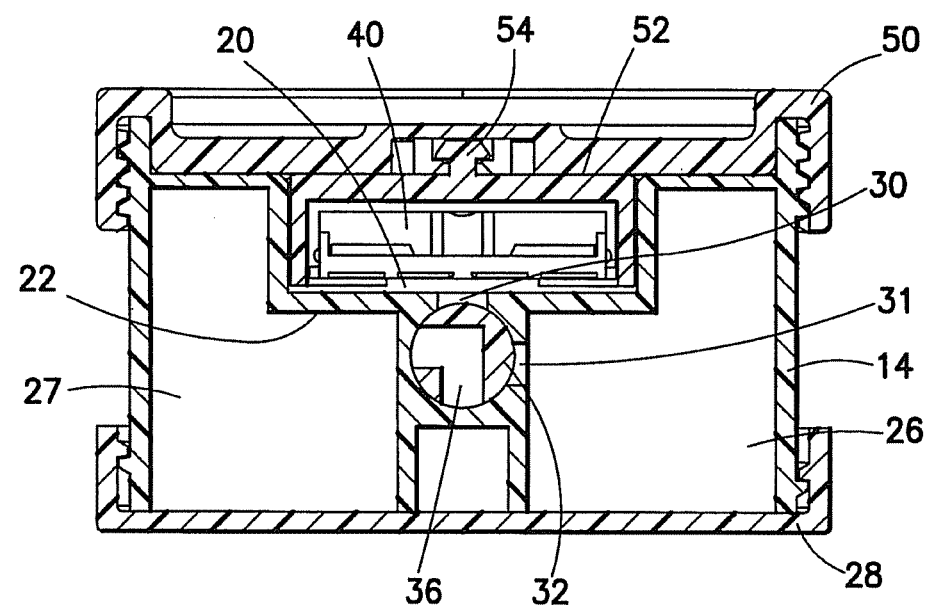
FIG. 6B is a cross-sectional view of the container as shown in FIG. 6A with the valve depicted in a closed position.
Figure 7A:
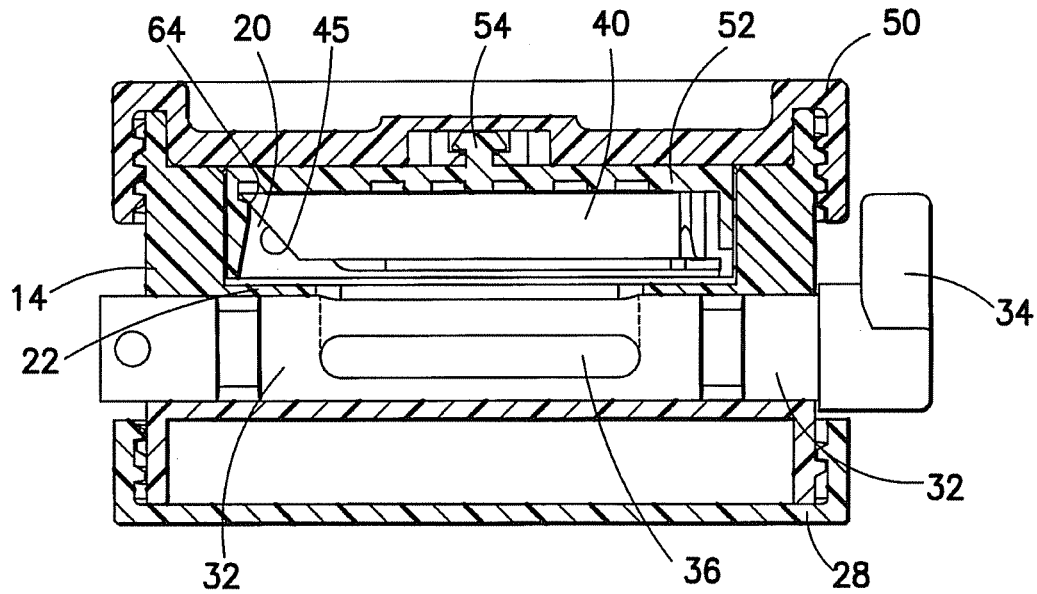
FIG. 7A is a cross-sectional view of the container taken along lines 7-7 of FIG. 1 with the valve depicted in an open position.
Figure 7B:
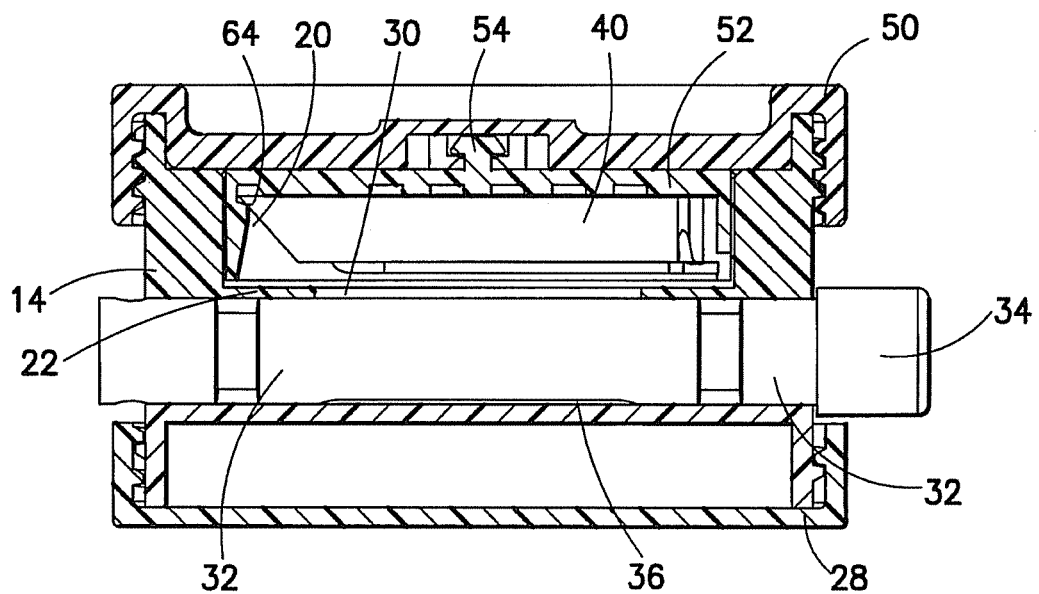
FIG. 7B is a cross-sectional view of the container as shown in FIG. 7A with the valve depicted in a closed position.
Figure 8:
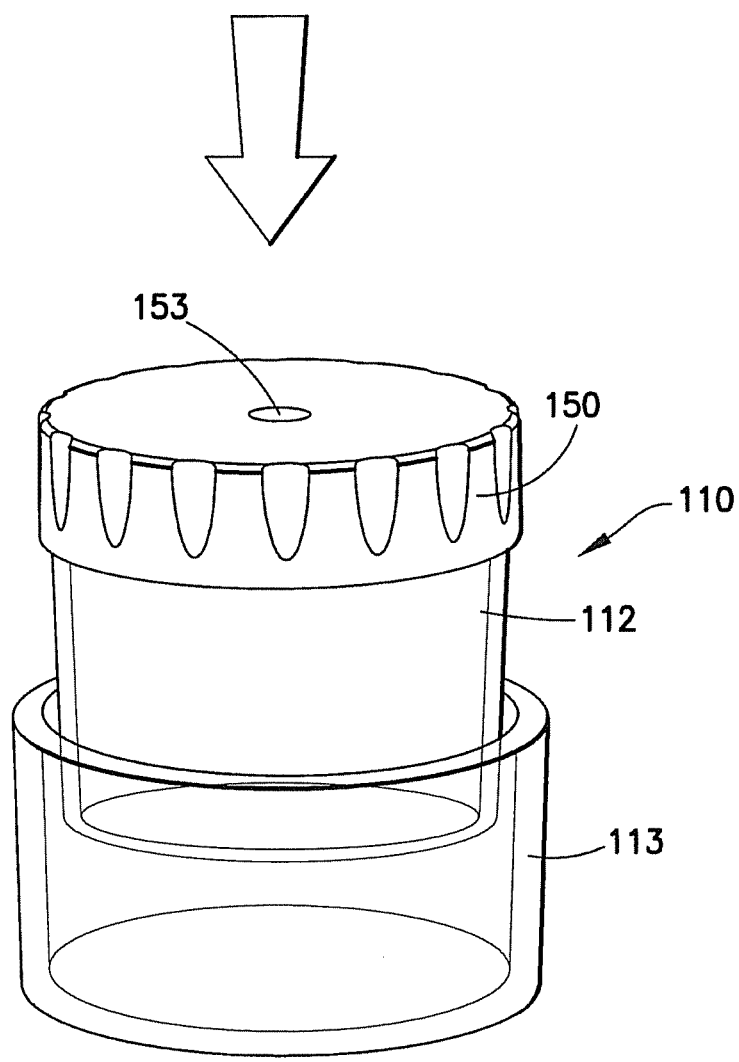
FIG. 8 is a perspective view of a container system for storing a biological sample in accordance with a further embodiment of the present invention.
Figure 9:
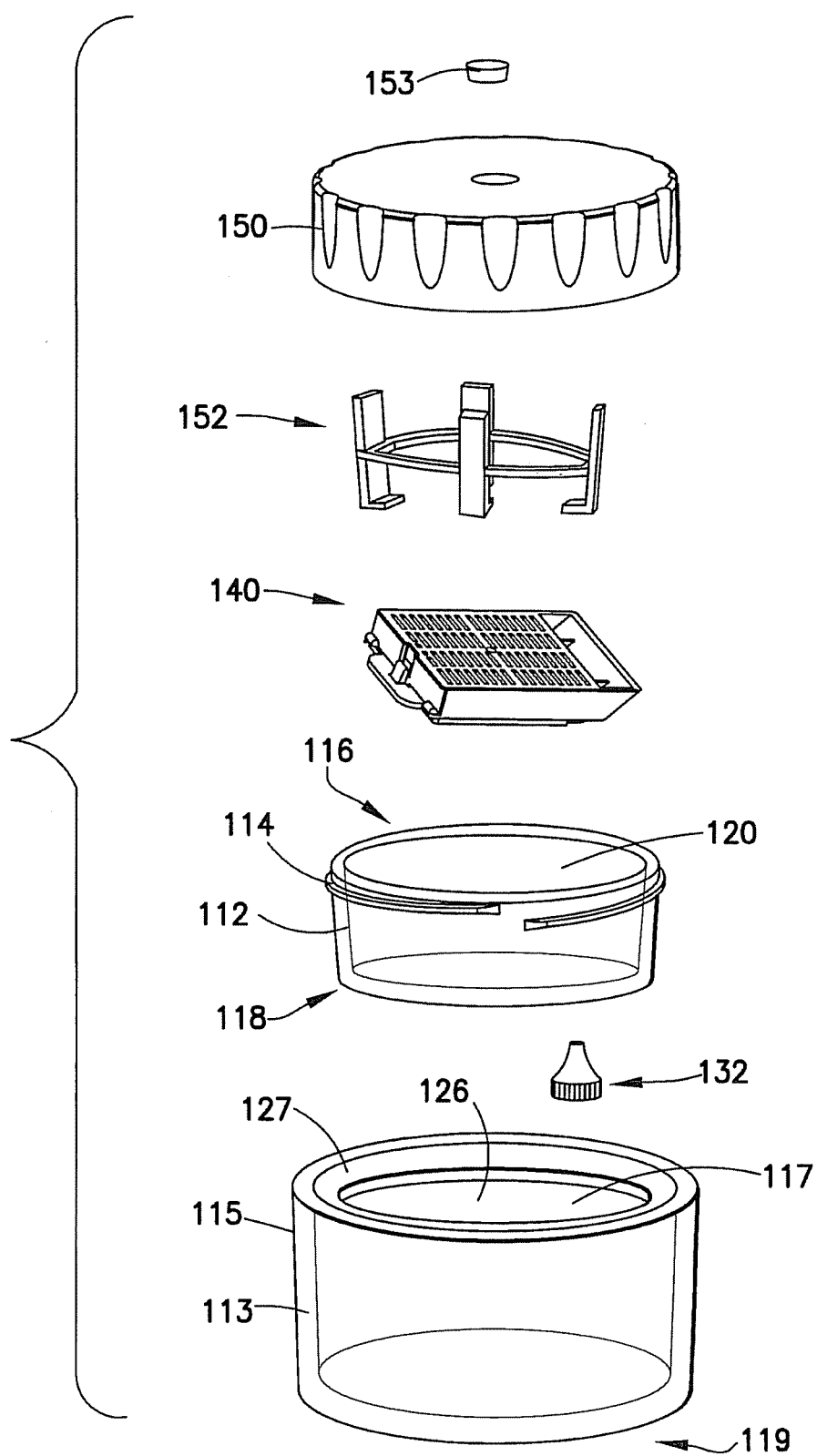
FIG. 9 is an exploded perspective view of the container of FIG. 8.
Figure 10:
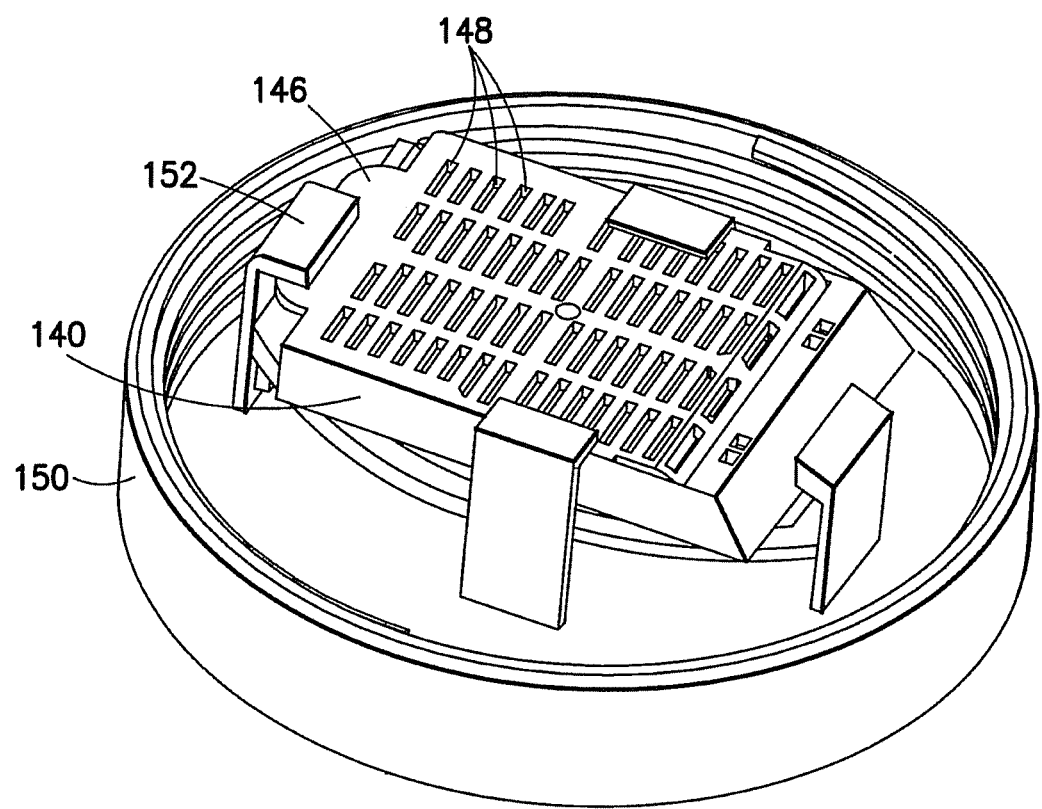
FIG. 10 is a bottom perspective view of a closure of the container of FIG. 8 in an embodiment of the present invention.

As discussed herein, valve 32 is movable between a first position where the first chamber 20 is in fluid isolation from the second chamber 26 (as shown in FIGS. 6B and 7B) and a second position wherein the first chamber 20 and second chamber 26 are in fluid communication (as shown in FIGS. 6A and 7A) such that fluid can pass at least from the second chamber 26 to the first chamber 20, and desirably can pass between both chambers.

Sample holder 40 is further provided for use with container 10, and is adapted to be received within first chamber 20 of housing 12. Sample holder 40 may form a part of container 10 or may be separately provided for use with container 10. Sample holder 40 may be in the form of a conventional histology cassette (a "histo-cassette") as is known in the art for storing a biological tissue sample during preparation of the sample for diagnostic testing. Such sample holders or histo-cassettes are known for containing biological specimens during processing with fluids to prepare the specimen for later analyses. Typically, such sample holders or histo-cassettes are generally rectangular, planar housing structures having an internal cavity, with a plurality of openings through the wall surface to provide fluid flow through the housing. Often, a removable or openable cover encloses the structure, such as through a hinge situated along one end of the housing structure for providing a door-like cover to the housing structure. Also, a planar surface, which may be slanted, is often provided in such sample holders or histo-cassettes, acting as a surface for labeling or writing. The dimensions for such a sample holder, for example, may include a height of about 0.3 inch (plus or minus 0.1 inch), a length of about 1.73 inches (plus or minus 0.1 inch), and a width of about 1.12 inches (plus or minus 0.1 inch). Examples of sample holders that may be useful herein are shown in U.S. Pat. No. 4,220,252 to Beall et al. and U.S. Pat. No. 4,034,884 to White, both of which are expressly incorporated herein by reference.

Figure 3A:
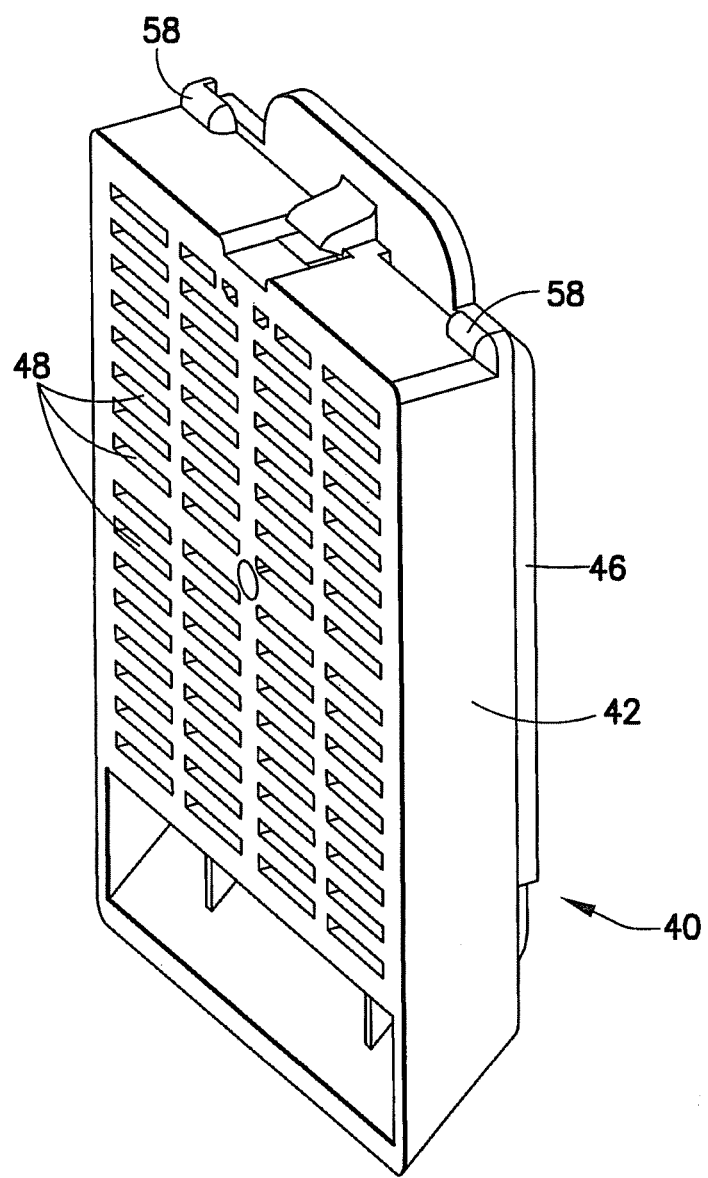
FIGS. 3A and 3B are perspective views of a sample holder of the container of FIG. 1 in an embodiment of the present invention, shown in a closed and an open position, respectively.
Figure 3B:
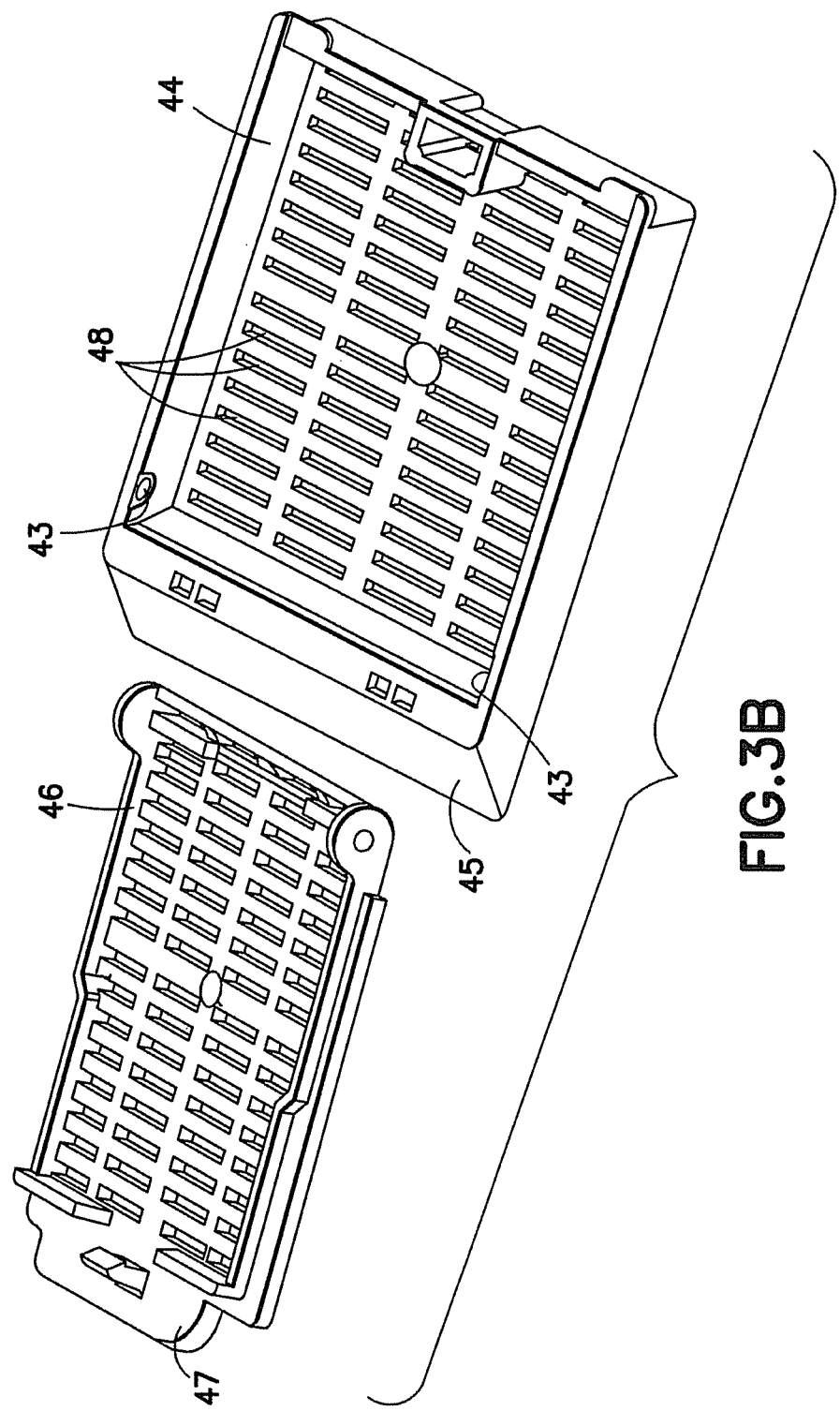

For example, as shown in FIGS. 3A and 3B, sample holder 40 includes a generally rectangular planar housing 42 having opposing walls defining an internal cavity 44 for holding a biological tissue sample therein. At least one of the walls of housing 42 may be slanted, such as slanted wall 45, providing a surface for applying a label or for writing, so as to provide a mechanism for identification of a sample contained within sample holder 40, as appropriate. Housing 42 of sample holder 40 is a closable structure, and may include a hinged door-like structure 46 attached with housing 42 thereby permitting access to the internal cavity 44 for storing a tissue sample within or removing a tissue sample from internal cavity 44. The door-like structure 46 may be integrally formed with housing 42 so as to provide a unitary structure with the door 46 connected to housing 42 through a flap to provide a mechanism for pivoting door 46 with respect to housing 42, or door 46 may be otherwise connectable to housing 42, such as through a pivot point 43 acting as a hinge for opening door 46 from one side of housing 42 to gain access to the internal cavity 44. Housing 42 of sample holder 40 includes at least one, and preferably a plurality of fluid openings 48 adapted to allow fluid to flow therethrough. In this manner, when housing 42 is positioned within first chamber 20, fluid within first chamber 20 can flow through openings 48 and contact the biological tissue sample contained within internal cavity 44.

Container 10 further includes closure 50 for enclosing the first open end 16 of housing 12. Closure 50 is matable with housing 12 at first open end 16 in any manner, such as a frictional fit, snap fit, threadable engagement, interlocking structural engagement, or other manner, providing a liquid tight seal. Desirably, closure 50 and housing 12 include corresponding threads such that closure 50 can be threaded with housing 12 to provide a liquid tight seal therebetween. For example, such corresponding threads may be provided about the perimeter of an external surface of closure 50 and within the perimeter of an internal surface of housing wall 14 of housing 12 at first end 16, or may be provided within the perimeter of an internal surface of closure 50 and about the perimeter of an external surface of housing wall 14 of housing 12 at first end 16.

Figure 4A:
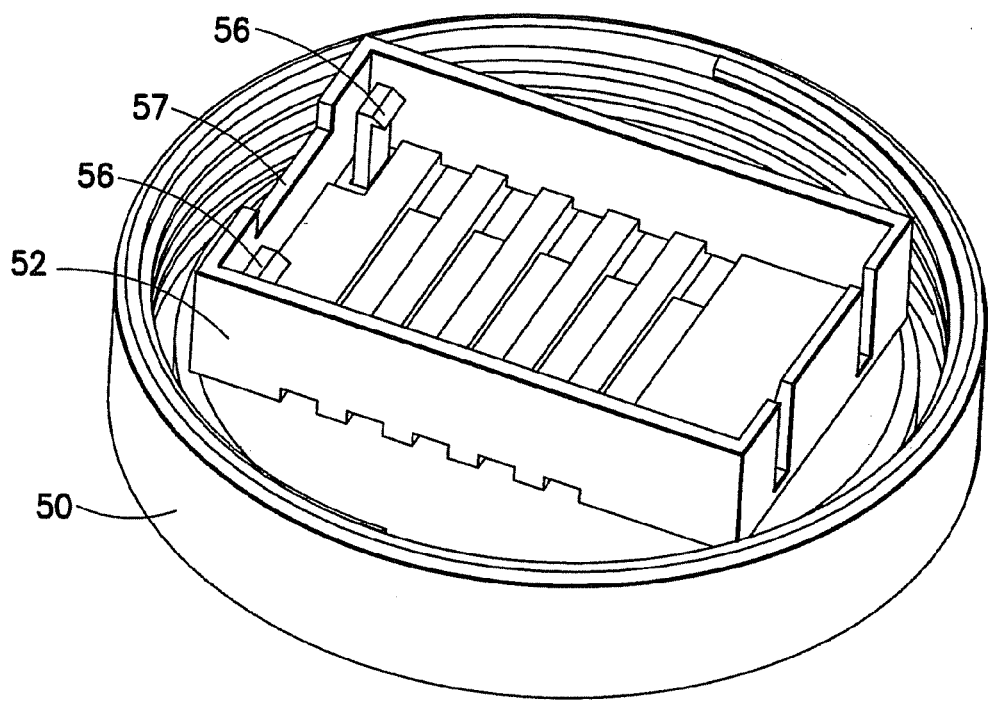
FIG. 4A is a perspective view of a closure of the container of FIG. 1 in an embodiment of the present invention.
Figure 4B:
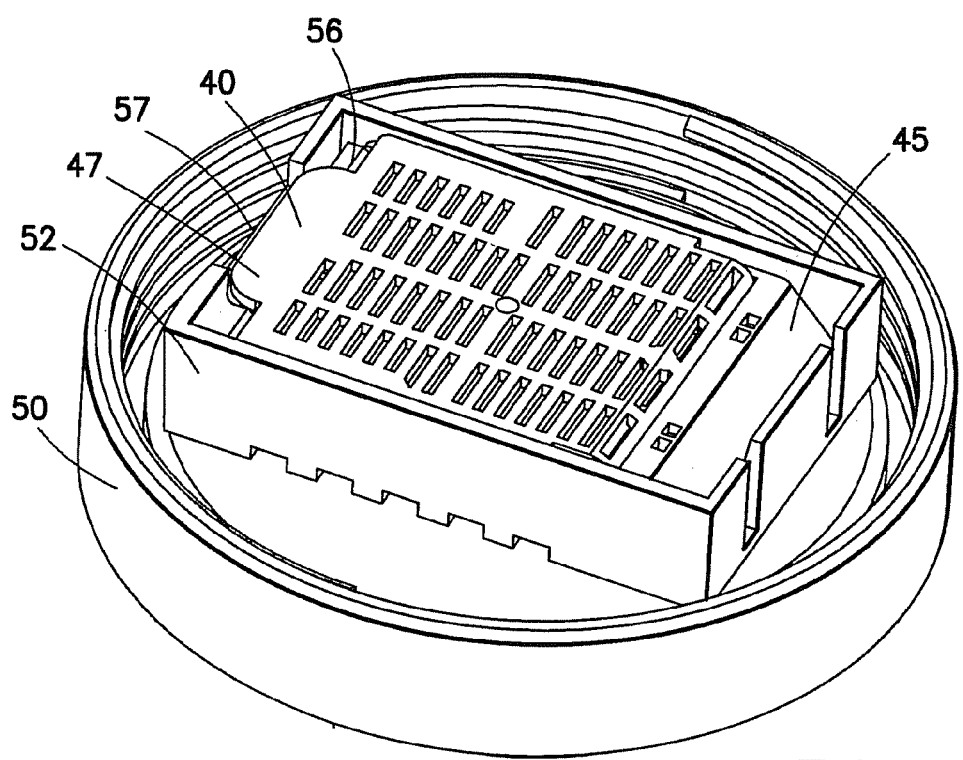
FIG. 4B is a perspective view of the closure of FIG. 4A including a sample holder therewith.

As noted, sample holder 40 may be provided as a separate element for use within first chamber 20 or may be interconnected with a part of container 10. Desirably, sample holder 40 is mated with closure 50. Such mating may be accomplished by providing sample holder 40 as an integral part connected to or formed with closure 50, or sample holder 40 may be a separate structure that is removably matable or detachably connected with closure 50. As shown in FIG. 4A, closure 50 may include a platform 52 extending from a bottom surface of closure 50, for accommodating sample holder 40 therein. Platform 52 may include structure for maintaining sample holder 40 attached to closure 50 as shown in FIG. 4B, such as in a snap-fit engagement, and sample holder 40 may be releasable from platform 52. In particular, platform 52 may be a generally rectangular structure defining a rectangular recess for accommodating the general size and shape of sample holder 40. Platform 52 may include one or more fingers 56 extending therefrom for engaging with sample holder 40, thereby maintaining sample holder 40 within the recess defined by platform 52. Such fingers 56 may be deflectable, such that when an edge of sample holder 40 adjacent the slanted wall 45 is held in place against a corresponding protrusion or finger (such as protrusion 64 shown in FIGS. 7A and 7B) of the platform 52, and sample holder 40 is pushed into the recess of platform 52, fingers 56 deflect away from the walls of sample holder 40 and then return to their initial position against nubs 58 of holder 40, thereby snapping sample holder 40 in place. Fingers 56 may lock sample holder 40 in place permanently with respect to platform 52 and closure 50 or may be deflectable so as to remove sample holder 40 from platform 52 if desired.

Platform 52 may also be provided with a general shape so as to permit opening of door 46 of sample holder 40 while maintaining housing 42 of sample holder 40 contained therein, thereby providing access to the interior cavity 44 of sample holder 40 while sample holder 40 is held in place within platform 52 and with respect to closure 50. For example, the wall surface of platform 52 may have a cut-away portion 57 to accommodating a handle-like protrustion 47 of door 46, and the overall dimensions and height of the walls of platform 52 may be designed so as to provide for manually opening of the door 46 by contact of handle 47 and pivoting of door 46 across platform 52 without interference.

In one embodiment, the platform may include mating structure capable of accommodating histo-cassettes or sample holders of different sizes and shapes. For example, as shown in an alternate embodiment depicted in FIGS. 15A-15E, platform 52a may include fingers 90a and 92a, which act as compressible elements for bearing against the wall surfaces of sample holders of various sizes. Such fingers 90a and 92a may act as biasing elements or leaf springs for exerting a biasing force against the wall surface of a sample holder placed within platform 52a biasing the sample holder against the sidewalls of platform 52a to hold the sample holder in place. More particularly, fingers 90a apply a biasing force against a sample holder contained within platform 52a, while opposing surface 91a holds an end of the sample holder therein and finger or protrusion 64a holds a separate edge of the sample holder therein. Also, finger 92a applies a biasing force against the sample holder while opposing protrusion 64a holds the end of the sample holder in place. Such opposite and equal forces assist in maintaining sample holders of various sizes and shapes in place. Further, wall cut-away portion 57a may also be provided, for accommodating a handle portion of the door of the sample holder, as discussed above, while also providing access to the handle portion for opening of the door while the sample holder is in place in the platform, if desired. In this manner, container 10 may be provided with a single platform that can accommodate various sizes and shapes of histo-cassettes therein for use with container 10. Additionally, platform 52a may include a plurality of holes 98a for fluid flow therethrough, as discussed above. Such holes 98a may include a pattern or orientation such that fluid flow through the platform to the sample holder will be sufficient for contact with a sample contained within the sample holder regardless of the size, shape and/or geometry of the sample holder.

As noted above, first chamber 20 may be sized so as to receive and accommodate sample holder 40 therein. In such an arrangement, when sample holder 40 is mated with closure 50 and closure 50 is rotatably engaged with housing 12, such as through a threaded engagement, sample holder 40 may be provided for rotation with respect to closure 50. This may be accomplished, for example, by providing platform 52 as a structure which is rotatable with respect to closure 50, such as through a pivoting connection 54, and by providing sample holder 40 within platform 52. In this manner, when sample holder 40 is placed within first chamber 20 and closure 50 is rotatably engaged with housing 12, one or both of the platform 52 and/or sample holder 40 will contact one or more of the side wall surfaces 24a-d upon rotation of closure 50, thereby maintaining sample holder 40 in place within first chamber 20 of housing 12 of container 10.

Container 10 may be assembled and provided with liquid media, such as solutions or reagents, stored within first chamber 20 and/or second chamber 26 at the point of manufacture. Alternatively, any such liquid media may be filled into the first chamber 20 and/or the second chamber 26 at any point prior to use, such as directly prior to inserting a tissue sample into sample holder 40.

As noted, container 10 may be provided for use with a one reagent system. In this manner, a single reagent solution, such as a tissue fixative like formalin, may be provided within second chamber 26. Such fixative solutions stabilize the RNA within a tissue sample, for conducting molecular diagnostic testing. Alternatively, container 10 may be provided for use with a two solution or a two reagent system. For example, a wash solution may be provided in second chamber 26, so as to dilute the first reagent fixative in the first chamber 20, or to deactivate the first reagent in the first chamber 20. It is also possible that each chamber contains the same reagent since it may be advantageous to refresh the same reagent after a period of time has passed. Or, a first reagent solution, such as a tissue fixative like formalin, may be used within first chamber 20, and a second reagent solution, such as a stabilizer in the form of a nucleic acid stabilization reagent for stabilizing the morphology of the tissue sample, may be provided within second chamber 26.

Any reagents may be used with the container of the present invention. For example, the fixative may be formalin, ethanol solutions, Carnoy's solution I (ethanol and acetic acid), Carnoy's Solution II (ethanol, chloroform and acetic acid), methacarn (methanol, chloroform and acetic acid), Clark's fixative, Boonfix, and the like. A non-limiting list of commercially available fixatives includes, but is not limited to, MIRSKY'S FIXATIVE (available from National Diagnostics, Inc. of Atlanta, Ga.); GLYOFIX (available from Shandon Lipshaw, Inc. of Pittsburgh, Pa.); HISTOCHOICE (available from Amresco); HISTOFIX (available from Trend Scientific, New Brighton, Minn.); KRYOFIX (available from Merck); MICROFIX (available from Energy Beam Sciences, Inc., East Granbury, Conn.); NEOFIX (available from Merck); NOTOX (available from Earth Safe Industries, Inc., Belle Mead, N.J.); OMNIFIX II and OMNIFIX 2000 (available from AnCon Genetics, Inc, Mellville, N.Y.); PREFER (available from Anatech Ltd, Battle Creek, Mich.); PRESERVE (available from Energy Beam Sciences, Inc., East Granbury, Conn.); SAFEFIX II (available from Thermo Fischer Scientific, Inc.); STATFIX (available from StatLab Medical Products, Inc. of Lewisville, Tex.); STF (Streck Tissue Fixative, available from Streck Laboratories, Omaha, Nebr.); UMFIX (available from Sakura Finetek USA, Inc., Torrance, Calif.); and FINEFIX (available from Milestone Medical of Shelton, Conn.). Commercially available stabilizers include, but are not limited to, RNALATER (available from Ambion, Inc., Austin Tex.); and RNEASY (available from Qiagen, Inc., Valencia, Calif.). Any other reagents known or hereafter discovered for use as fixatives and/or stabilizers are intended as useful in the present invention.

To assemble container 10, valve 32 is placed in the closed position, and second chamber 26 is filled with the desired liquid medium. In embodiments where second end 18 is a closed end, such liquid medium can be supplied within second chamber 26 through a port or opening, or may be supplied through first open end 16, that is through first chamber 20 and through openings 30, 31 when valve 32 is in an open position, prior to closing valve 32. Alternatively, housing 12 is provided with an open second end 18, with cover 28 placed over second end 18 and mated therewith after filling second chamber 26 to contain the liquid medium within second chamber 26. Thereafter, first chamber 20 may be filled with a second liquid medium (for example, in embodiments involving a two reagent system) through first open end 16. Closure 50, with or without sample holder 40 extending therefrom, is then placed over the first open end 16 of housing 12 and threadably mated therewith. The container 10 thus assembled may be packaged in a separate package, if desired, and stored for use.

In use, a biological sample, such as a tissue sample extracted from a patient for molecular or histology diagnostics testing, is placed within cavity 44 within sample holder 40, such as through the hinged door 46. In embodiments where sample holder 40 is provided as a separate element, closure 50 can be removed from housing 12 and sample holder 40 may then be inserted into the platform 52 of closure 50. Alternatively, if sample holder 40 is provided with closure 50, the tissue sample may be placed within sample holder 40 after closure 50 is removed from housing 12, either with sample holder 40 connected thereto or by removing sample holder 40 therefrom and then reattaching it thereto.

Closure 50, with sample holder 40 containing the tissue sample therein, is thereafter placed over the first open end 16 of housing 12, with sample holder 40 aligned within and placed into first chamber 20. Closure 50 is then mated with housing 12, such as by rotating closure 50 and/or housing 12 with respect to each other in a threaded engagement. During such respective rotation, sample holder 40 can maintain its orientation within first chamber 20 in embodiments in which first chamber 20 is sized and oriented for accommodating the particular shape of sample holder 40 as discussed above.

In embodiments including a one reagent system as discussed above, the tissue sample at this point is contained within sample holder 40 in first chamber 20 in isolation from the reagent within second chamber 26. When it is desired to contact the tissue sample with the reagent, valve 32 may be opened, such as through a user turning handle 34, thereby moving the fluid channel 36 of valve 32 from a first orientation to prevent fluid communication between the first chamber 20 and the second chamber 26 (as shown in FIGS. 6B and 7B) to a second orientation where the fluid channels are aligned between the first chamber 20 and the second chamber 26 (as shown in FIGS. 6A and 7A) to provide fluid communication therebetween. Container 10 may then be inverted, shaken, or otherwise moved so as to cause the reagent within second chamber 26 to flow through the fluid channel 36 of valve 32 and into first chamber 20, thereby flowing through the fluid openings of sample holder 40 to contact the tissue sample contained within cavity 44 therein. By maintaining the tissue sample separated from the reagent contained within the second chamber 26 in this manner, contact between the sample and the reagent can be precisely regulated until a desired time, and the length of time of contact of the tissue sample and the reagent can be precisely regulated and monitored.

It is further contemplated that a one reagent system can be used wherein the reagent is placed within the first chamber 20 and the tissue sample is immediately contacted with the tissue sample when placed within the first chamber 20, and after contact for a desired time period valve 32 may be opened so as to drain the reagent from the first chamber 20 into the second chamber 26, thereby isolating the tissue sample from further contact with the reagent.

In embodiments including a two reagent system as discussed above, when the sample holder 40 is placed within first chamber 20, the tissue sample is placed in contact with the first reagent contained within first chamber 20, with such reagent flowing through the fluid openings 48 of sample holder 40, thereby contacting the tissue sample contained within the internal cavity 44 thereof. The tissue sample can be maintained in contact with the reagent within the first chamber 20 for a specified time period, after which time the valve may be opened so as to cause fluid flow between the first chamber 20 and the second chamber 26. Thus, the second reagent maintained within second chamber 26 can flow through the fluid channel 36 of valve 32 and into first chamber 20, thereby contacting the tissue sample contained therein. Moreover, it is contemplated that the first reagent within the first chamber 20 will likewise flow through valve 32 into the second channel, thereby mixing with the second reagent. Accordingly, the concentrations of the first and second reagents can be specifically tailored so as to ensure that any mixing of the two reagents will not have a deleterious effect on the intended functionality of the reagent when contacted with the tissue sample. After the second reagent is displaced into first chamber 20 and contacted with the tissue sample for a desired time period, the closure 50 may be removed so as to remove the tissue sample from sample holder 40 for any desired diagnostic testing.

It also contemplated that a third chamber may be provided within housing 12, such as within dead space 27. In this manner, valve 32 can be selectively positionable between a first position where first chamber 20 and second chamber 26 are in fluid isolation, a second position where first chamber 20 is in fluid communication with dead space 27, and a third position where first chamber is in fluid communication with second chamber 26. In this manner, when the valve 32 is in the first position, first chamber 20 is a closed environment, and the tissue sample can be maintained in contact with the reagent within the first chamber 20 for a specified time period, after which time the valve may be moved to the second position, so as to cause fluid flow between the first chamber 20 and the empty chamber defined by dead space 27. Thus, the fluid contained within first chamber 20 can be drained into the dead space 27, and the valve can thereafter be moved to the third position, such that fluid communication is established between the second chamber 26 and the first chamber 20, thereby permitting the second reagent maintained within second chamber 26 to flow through the fluid channel 36 of valve 32 and into first chamber 20, thereby contacting the tissue sample contained therein.

Since sample holder 40 is connected with closure 50, access to the tissue sample contained within sample holder 40 can be achieved by removing closure 50 from container 10 and inverting it, placing the outer surface on a counter, thereby preventing sample holder 40 from being exposed. Any fluid that is contained within sample holder 40 can drip downward within the bottom or internal surface of closure 50 and be caught by the rim surrounding closure 50, thereby preventing any leakage or spillage onto the counter surface. The hinged door 46 of sample holder 40 may be openable with the sample holder 40 connected with the closure 50, such as through platform 52, thereby providing a simple access to the tissue sample contained therein, and providing a proper support for maintaining the sample holder 40 in place without having to physically contact any portion of the sample holder (other than the edge of the door 46 at handle 47) to hold it in place while accessing the sample, thereby preventing any potential for contamination of the sample based on contact by the user.

Thereafter, the container 10 may be washed and re-used, or more preferably, will be discarded to prevent cross-contamination with other samples.

In a further embodiment shown in FIGS. 8-14, the container 110 includes a first housing 112 including a housing wall 114 extending between a first open end 116 and a generally closed second end 118. First housing 112 defines first chamber 120, with first open end 116 extending into the first chamber 120. First chamber 120 defines a first intended fill volume, and may include a cavity that may be sized so as to receive and accommodate sample holder 140 therein.

In the embodiment shown in FIGS. 8-14, container 110 further includes a second housing 113 having a housing wall 115 extending between a first open end 117 and a second closed end 119. Second housing 113 defines second chamber 126 defining a second intended fill volume, which is desirably different than the first intended fill volume of the first chamber 120. First open end 117 of second housing 113 is sized so as to accommodate second end 118 of first housing 112 insertably therein. As such, first open end 117 of second housing 113 may include an annular shoulder lip 127 extending within an inner perimetrical surface of first open end 117 and defining an opening 129 therein. Shoulder lip 127 may be provided as an o-ring, and is desirably a flexible member that permits first housing 112 to be inserted through opening 129 and into second housing 113 in sealed arrangement with shoulder lip 127 sliding along the outer housing wall 114, as will be discussed in more detail herein.

Container 110 further includes sample holder 140, as described in connection with the embodiment of FIGS. 1-7. In particular, sample holder 140 is adapted to be received within first chamber 120 of first housing 112, such as a conventional histo-cassette, including a closable housing 142 defining an internal cavity (not shown) for holding a biological tissue sample, with access provided through a hinged door-like structure 146, and with at least one, and preferably a plurality of fluid openings 148 adapted to allow fluid to flow therethrough.

Container 110 further includes closure 150 for enclosing the first open end 116 of first housing 112. Closure 150 is matable with first housing 112 at first open end 116 in a similar manner as described in connection with the embodiment of FIGS. 1-7. Desirably, closure 150 and first housing 112 include corresponding threads such that closure 150 can be threaded with first housing 112 to provide a liquid tight seal therebetween. Furthermore, closure 150 may include a platform 152 extending from a bottom surface of closure 150, for accommodating sample holder 140 therein, as described above in connection with the embodiment of FIGS. 1-7.

Figure 11:
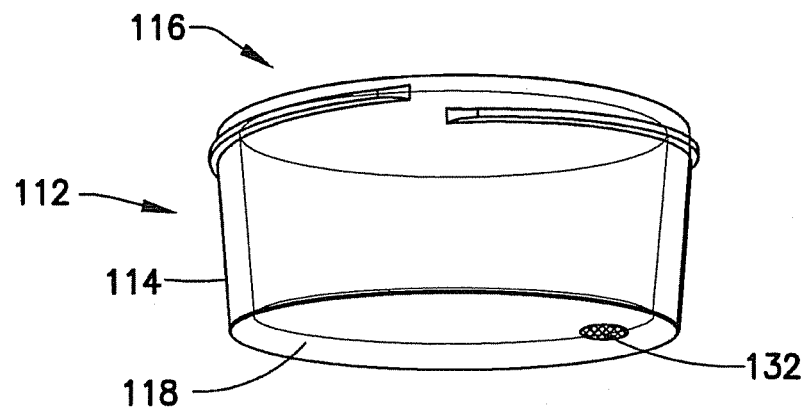
FIG. 11 is a bottom perspective view of a first housing of the container of FIG. 8.
Figure 12:
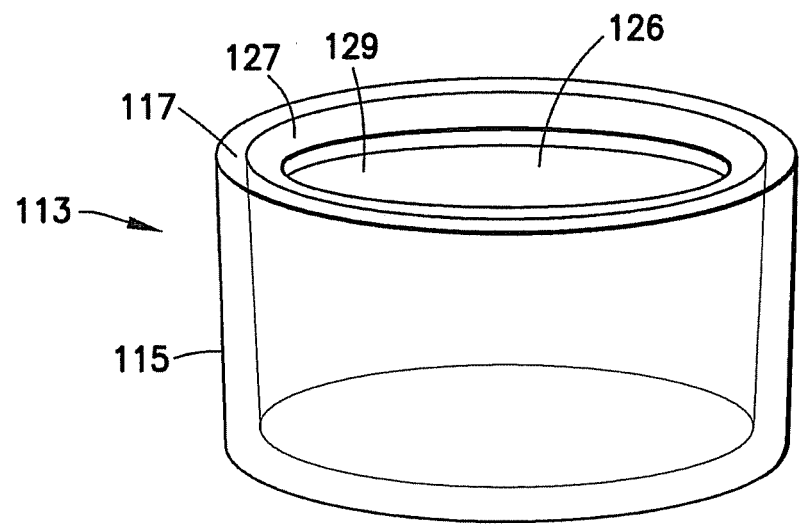
FIG. 12 is a perspective view of a second housing of the container of FIG. 8.

Container 110 includes structural features such that first chamber 120 defined by first housing 112 and second chamber 126 defined by second housing 113 may be selectively placed in fluid communication with each other. As shown in FIG. 11, this may be accomplished by providing a valve 132 within the second end 118 of first housing 112, acting as a transitional barrier between the first housing 112 and the second housing 113. For example, valve 132 can extend through housing wall 114 of first housing 112. Valve 132 may be a one-way valve, such as a "duck-bill" type valve, for permitting fluid flow in only one direction, such as into first chamber 120 but not out of first chamber 120. Alternatively, valve 132 may permit fluid flow in both directions, such as into first chamber 120 and out of first chamber 120. It is also contemplated that first housing 112 may include a venting outlet for venting fluid, such as trapped air, out from first chamber 120. For example, a porous vent outlet 153 may be providing on closure 150, and adapted for venting air therethrough, but preventing liquid flow therethrough. It is contemplated that such a vent outlet can be provided within first housing 112 as opposed to closure 140, so long as it is capable of venting from first chamber 120. Vent outlet 153 may also be provided as a one-way vent, so as to permit air to vent out of first chamber 120 to ambient, while preventing any ambient air or fluid from passing therethrough into the first chamber 120.

Figure 13:
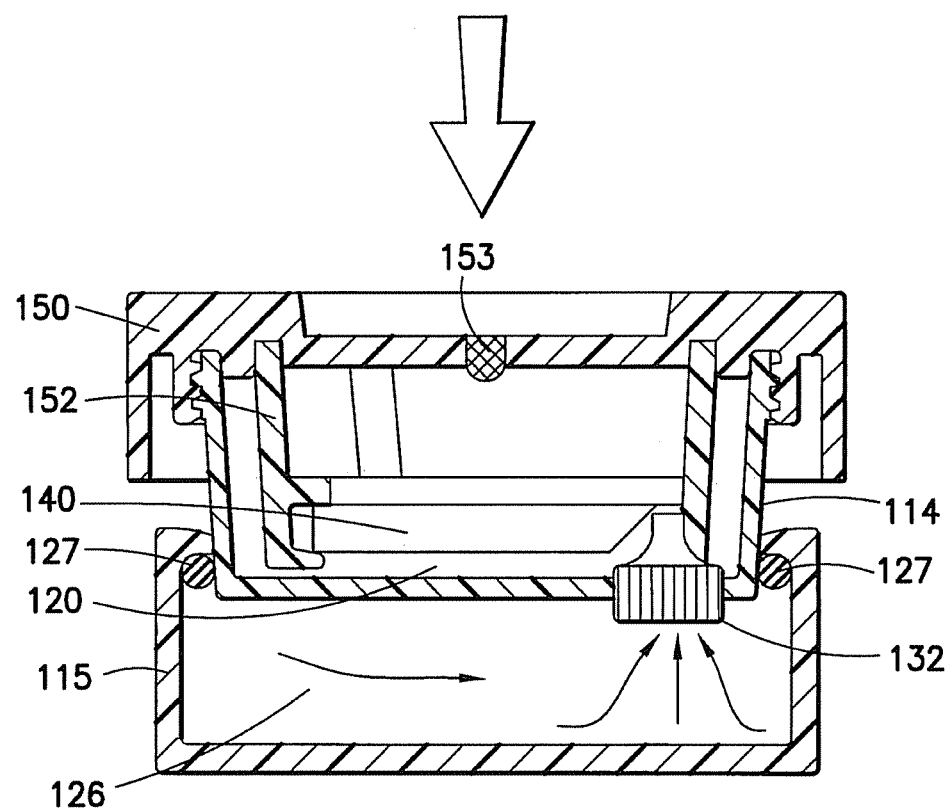
FIG. 13 is a side sectional view of the container system shown in FIG. 8 in a first position with the first housing positioned at the open end of the second housing.
Figure 14:
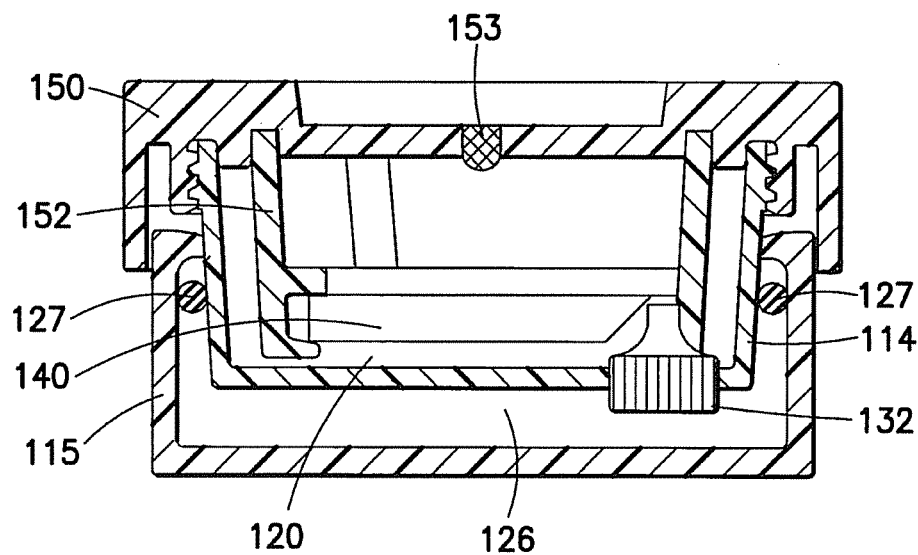
FIG. 14 is a side sectional view of the container system shown in FIG. 8 shown in a second position with the first housing inserted within the second housing.
Figure 15C:
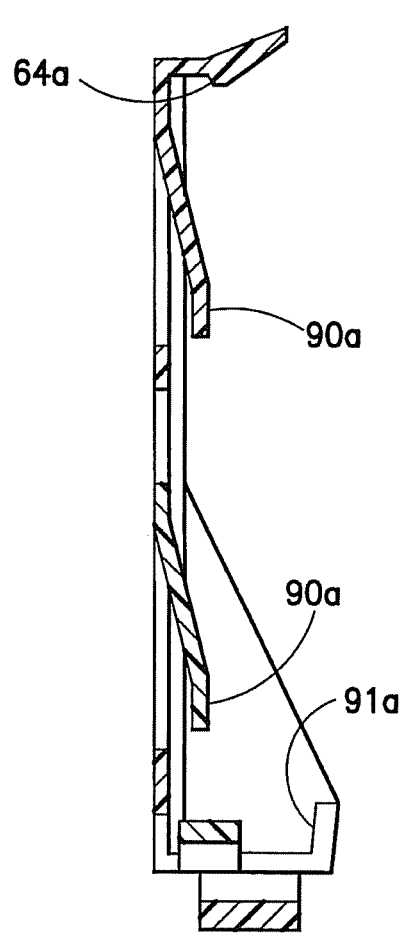
FIG. 15C is a side sectional view of the platform taken along line A-A of FIG. 15B.
Figure 15D:
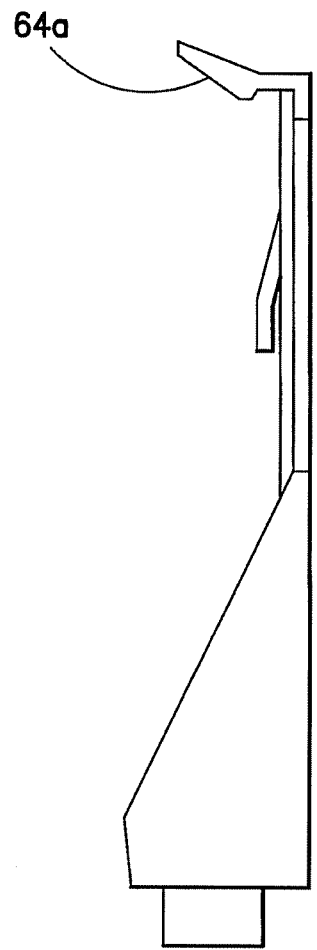
FIG. 15D is a side view of the platform of FIG. 15A.
Figure 15E:
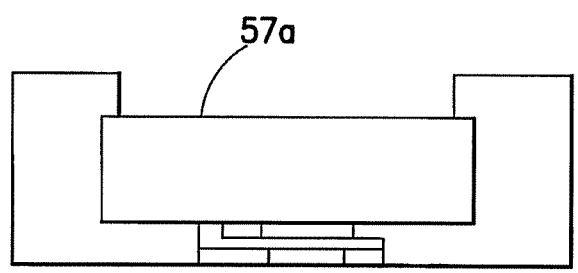
FIG. 15E is a top view of the platform of FIG. 15A.

Container 110 may be assembled and provided with liquid media, such as solutions or reagents, stored within first chamber 120 and/or second chamber 126, at the point of manufacture. Alternatively, any such liquid media may be filled into the first chamber 120 and/or the second chamber 126 at any point prior to use, such as directly prior to inserting a tissue sample into sample holder 140. Desirably, container 110 is provided with first housing 112 in a first position with respect to second housing 113, as depicted in FIG. 13, and fixed in such a position, such as through a friction fit or other mechanical engagement between the first housing 112 and the second housing 113.

In use, a biological sample, such as a tissue sample extracted from a patient for molecular or histology diagnostics testing, is placed within cavity 144 within sample holder 140 as discussed above. Closure 150 with sample holder 140 containing the tissue sample therein is thereafter placed over the first open end 114 of first housing 112, with sample holder 140 placed into first chamber 120. Closure 150 is then mated with first housing 112, such as by rotating closure 150 and/or housing 112 with respect to each other in a threaded engagement. During such respective rotation, sample holder 140 may freely move within first chamber 120, or can maintain its orientation within first chamber 120 in embodiments in which first chamber 120 is sized and oriented for accommodating the particular shape of sample holder 140 as discussed above.

In embodiments including a one reagent system as discussed above, the tissue sample at this point is contained within sample holder 140 in first housing 112 in isolation from the reagent within second housing 113. When it is desired to contact the tissue sample with the reagent, first housing 112 is inserted within second housing 113 (or inserted further within the second housing 113), such as by pushing downwardly, causing the outer surface of housing wall 114 to ride along the flexible membrane of shoulder lip 127 to the position of FIG. 14. During such movement, the reagent contained within the second chamber 126 of second housing 113 is displaced or forced through valve 132 and into first chamber 120 of first housing 112. To facilitate such fluid movement or displacement, air within first chamber 120 is vented out to atmosphere through vent outlet 153. In this manner, the reagent within second chamber 126 flows through the valve 132 and into first chamber 120, thereby flowing through the fluid openings 148 of sample holder 140 to contact the tissue sample contained within cavity (not shown) therein.

In embodiments including a two reagent system, when the sample holder 140 is placed within first housing 112, the tissue sample is placed in contact with the first reagent contained within first chamber 120, with such reagent flowing through the fluid openings 148 of sample holder 140, thereby contacting the tissue sample contained within the internal cavity 144 thereof. The tissue sample can be maintained in contact with the reagent within the first chamber 120 for a specified time period, after which time the first housing 112 is inserted within the second housing 113 (or inserted further within the second housing 113), such as by pushing downwardly as described above. Doing so causes the second reagent maintained within second chamber 126 of second housing 113 to flow through the valve 132 and into first chamber 120 of first housing 112, thereby contacting the tissue sample contained therein.

While embodiments of the present invention are satisfied in many different forms, there is shown in the figures and described herein in detail, specific embodiments of the invention, with the understanding that the present disclosure is to be considered as exemplary of the principles of the invention and is not intended to limit the invention to the embodiments illustrated. Various other embodiments will be apparent to, and readily made by those skilled in the art, without departing from the scope and spirit of the invention. The scope of the invention will be measured by the appended claims and their equivalents.

What is claimed is:

1. A container for storing a biological sample, comprising:
   a first chamber having an open end and structured to receive a fluid;
   a sample holder at least partially disposed within the first chamber;
   a second chamber adapted to receive a fluid therein;
   a closure for enclosing at least the open end of the first chamber; and
   a transitional barrier disposed at least partially between the first chamber and the second chamber, the transitional barrier configured for controlling passage of fluid between the first chamber and the second chamber,
   wherein the sample holder is detachably connected to the closure,
   wherein the sample holder is rotatable with respect to the closure, when the sample holder is mated to the closure and when the closure is engaged with the open end; and
   wherein the transitional barrier is transitional from a first position in which the first chamber is in fluid isolation from the second chamber, to a second position in which fluid can pass from at least one of the first chamber and the second chamber to the other of the first chamber and the second chamber.

2. The container of claim 1, further comprising a platform attached to the closure and adapted for receiving the sample holder.

3. The container of claim 2, wherein the platform is rotatable with respect to the closure.

4. The container of claim 1, wherein the sample holder comprises a closable housing defining an internal cavity for holding a biological sample, the housing comprising a plurality of fluid openings for allowing fluid contained within at least one of the first chamber and the second chamber to pass into the internal cavity.

5. The container of claim 1, wherein the sample holder is a histology cassette.

6. The container of claim 1, wherein the first chamber has a first intended fill volume and the second chamber has a second intended fill volume different than the first intended fill volume.

7. The container of claim 1, further comprising a first fluid disposed within the first chamber and a second fluid disposed within the second chamber, wherein the first fluid is different than the second fluid.

8. The container of claim 1, wherein the transitional barrier is a valve.

9. The container of claim 8, wherein the valve comprises a handle for movement of the valve between the first position and the second position.

10. A container for storing a biological sample, comprising:
- a housing extending between a first open end and a second end, the first open end defining a first chamber adapted to receive a fluid, the housing further comprising a second chamber adapted to receive a fluid therein;
- a sample holder at least partially disposed within the first chamber;
- a closure for enclosing at least the first open end of the housing; and
- a valve extending between the first and second chambers, wherein the valve is movable between a first position in which the first chamber is in fluid isolation from the second chamber, to a second position in which fluid can pass from at least the second chamber into the first chamber,
- wherein the sample holder is detachably connected to the closure, and
- wherein the sample holder is rotatable with respect to the closure, when the sample holder is mated to the closure and when the closure is engaged with the first open end.

11. The container of claim 10, wherein the sample holder extends from the closure into the first chamber, the sample holder defining an internal cavity for holding a biological sample and comprising at least one fluid opening adapted for allowing fluid contained within at least one of the first chamber and the second chamber to pass into the internal cavity.

12. The container of claim 10, wherein the closure and the housing are removably provided in threaded engagement.

13. The container of claim 10, wherein the valve comprises a handle for movement of the valve between the first position and the second position.

14. A container for storing a biological sample, comprising:
- a first chamber having an open end and structured to receive a fluid;
- a sample holder at least partially disposed within the first chamber;
- a second chamber adapted to receive a fluid therein;
- a closure for enclosing at least the open end of the first chamber; and
- a rotatable valve disposed at least partially between the first chamber and the second chamber, the rotatable valve configured for controlling passage of fluid between the first chamber and the second chamber,
- wherein the sample holder is detachably connected to the closure, and
- wherein the sample holder is rotatable with respect to the closure, when the sample holder is mated to the closure and when the closure is engaged with the open end.

* * * * *